(12) United States Patent
Evans et al.

(10) Patent No.: US 10,450,287 B2
(45) Date of Patent: Oct. 22, 2019

(54) PROCESSES AND SYSTEMS FOR REMOVING AN ALKYL IODIDE IMPURITY FROM A RECYCLE GAS STREAM IN THE PRODUCTION OF ETHYLENE OXIDE

(71) Applicant: SHELL OIL COMPANY, Houston, TX (US)

(72) Inventors: Wayne Errol Evans, Richmond, TX (US); Jesse Raymond Black, Houston, TX (US)

(73) Assignee: SHELL OIL COMPANY, Houston, TX (US)

(*) Notice: Subject to any disclaimer, the term of this patent is extended or adjusted under 35 U.S.C. 154(b) by 0 days.

(21) Appl. No.: 16/061,787

(22) PCT Filed: Dec. 13, 2016

(86) PCT No.: PCT/EP2016/080749
§ 371 (c)(1),
(2) Date: Jun. 13, 2018

(87) PCT Pub. No.: WO2017/102698
PCT Pub. Date: Jun. 22, 2017

(65) Prior Publication Data
US 2018/0370936 A1    Dec. 27, 2018

(30) Foreign Application Priority Data
Dec. 15, 2015 (EP) .................................. 15200267

(51) Int. Cl.
*C07D 301/32* (2006.01)
*C07C 17/38* (2006.01)
(Continued)

(52) U.S. Cl.
CPC ....... *C07D 301/32* (2013.01); *B01D 53/0423* (2013.01); *B01D 53/70* (2013.01);
(Continued)

(58) Field of Classification Search
CPC .. C07D 301/32; C07D 301/10; C07D 303/04; C07C 29/12; C07C 17/389; C07C 17/38;
(Continued)

(56) References Cited

U.S. PATENT DOCUMENTS 2,289,063 A   7/1942   Ocon et al.
3,573,201 A   3/1971   Annesser et al.
(Continued)

FOREIGN PATENT DOCUMENTS

DE   202012012866 U1   2/2014
EP         0776890 A2   6/1997
(Continued)

OTHER PUBLICATIONS

International Search Report and Written Opinion received for PCT Patent Application No. PCT/EP2016/080744, dated Mar. 14, 2017, 12 pages.
(Continued)

*Primary Examiner* — Taylor V Oh
(74) *Attorney, Agent, or Firm* — James D. Carruth

(57) ABSTRACT

Processes for reducing the amount of a gaseous iodide-containing impurity present in a recycle gas stream used in the production of ethylene oxide, in particular an alkyl iodide impurity, are provided. Processes for producing ethylene oxide, ethylene carbonate and/or ethylene glycol, and associated reaction systems are similarly provided.

16 Claims, 4 Drawing Sheets

(51) Int. Cl.

| | | |
|---|---|---|
| *C07C 17/389* | (2006.01) | |
| *C07C 29/12* | (2006.01) | |
| *B01D 53/04* | (2006.01) | |
| *B01D 53/70* | (2006.01) | |
| *C07D 301/10* | (2006.01) | |
| *C07D 303/04* | (2006.01) | |

(52) U.S. Cl.
CPC ............ *C07C 17/38* (2013.01); *C07C 17/389* (2013.01); *C07C 29/12* (2013.01); *C07D 301/10* (2013.01); *C07D 303/04* (2013.01); *B01D 2253/104* (2013.01); *B01D 2253/1122* (2013.01); *B01D 2257/2068* (2013.01)

(58) Field of Classification Search
CPC ...... B01D 2253/104; B01D 2253/1122; B01D 2257/2068
USPC ........................................................ 549/542
See application file for complete search history.

(56) References Cited

U.S. PATENT DOCUMENTS

| | | |
|---|---|---|
| 4,048,096 A | 9/1977 | Bissot |
| 4,761,394 A | 8/1988 | Lauritzen |
| 4,766,105 A | 8/1988 | Lauritzen |
| 4,789,528 A | 12/1988 | Owen et al. |
| 5,179,057 A | 1/1993 | Bartley |
| 5,189,004 A | 2/1993 | Bartley |
| 5,380,697 A | 1/1995 | Matusz et al. |
| 5,739,075 A | 4/1998 | Matusz |
| 6,040,467 A | 3/2000 | Papavassiliou et al. |
| 6,368,998 B1 | 4/2002 | Lockemeyer |
| 6,656,874 B2 | 12/2003 | Lockemeyer |
| 7,030,056 B2 | 4/2006 | Birke et al. |
| 7,193,094 B2 | 3/2007 | Chipman et al. |
| 7,425,647 B2 | 9/2008 | Lemanski et al. |
| 8,546,592 B2 | 10/2013 | Evans et al. |
| 8,921,586 B2 | 12/2014 | Matusz |
| 8,932,979 B2 | 1/2015 | Matusz et al. |
| 2003/0204101 A1 | 10/2003 | Jewson et al. |
| 2006/0070918 A1 | 4/2006 | Seapan et al. |
| 2007/0173655 A1 | 7/2007 | Grey |
| 2008/0281118 A1 | 11/2008 | Matusz |
| 2009/0050535 A1 | 2/2009 | Evans |
| 2009/0292132 A1 | 11/2009 | Evans |
| 2011/0034710 A1 | 2/2011 | Matusz |
| 2014/0001089 A1 | 1/2014 | Bazer-Bachi et al. |
| 2017/0291119 A1 | 10/2017 | Wilkinson et al. |

FOREIGN PATENT DOCUMENTS

| | | |
|---|---|---|
| EP | 2279182 A1 | 2/2011 |
| GB | 2107712 A | 5/1983 |
| WO | 9908790 A1 | 2/1999 |
| WO | 9908791 A1 | 2/1999 |
| WO | 2008144402 A2 | 11/2008 |
| WO | 2009021830 A1 | 2/2009 |
| WO | 2009140319 A1 | 11/2009 |
| WO | 2012071052 A1 | 5/2012 |
| WO | 2016001348 A1 | 1/2016 |
| WO | 2017102694 A1 | 6/2017 |
| WO | 2017102698 A1 | 6/2017 |
| WO | 2017102701 A1 | 6/2017 |

OTHER PUBLICATIONS

International Search Report and Written Opinion received for PCT Patent Application No. PCT/EP2016/080749, dated Feb. 17, 2017, 8 pages.
International Search Report and Written Opinion received for PCT Patent Application No. PCT/EP2016/080752, dated Apr. 4, 2017, 9 pages.
International Search Report and Written Opinion received for PCT Patent Application No. PCT/EP2016/080759, dated Apr. 4, 2017, 9 pages.
Evans et al., "Industrial Epoxidation Processes", Industrial Epoxidation Processes, Encyclopedia of Catalysis (Wiley—Interscience), 2003, vol. 3, pp. 246-264.
Brunauer et al., "Adsorption of Gases in MultiMolecular Layers", Journal of American Chemical Society, Feb. 1938, vol. 60, Issue No. 2, pp. 309-319.
Kirk-Othmer, Encyclopedia of Chemical Technology, 4th Edition, vol. 9, pp. 915-959.
Grant et al., "Grant & Hach's Chemical Dictionary", MacGraw-Hill Book Co., 1987, p. 433.

US 10,450,287 B2

PROCESSES AND SYSTEMS FOR REMOVING AN ALKYL IODIDE IMPURITY FROM A RECYCLE GAS STREAM IN THE PRODUCTION OF ETHYLENE OXIDE

CROSS REFERENCE TO RELATED APPLICATIONS

This is a national stage application of International application No. PCT/EP2016/080749, filed 13 Dec. 2016, which claims benefit of priority of European application No. 15200267.1, filed 15 Dec. 2015.

FIELD OF THE INVENTION

The present invention relates to a process and reaction system for the preparation of ethylene oxide, ethylene carbonate and/or ethylene glycol from ethylene.

BACKGROUND

Monoethylene glycol is used as a raw material in the manufacture of polyester fibres, polyethylene terephthalate (PET) plastics and resins. It is also incorporated into automobile antifreeze liquids. Ethylene carbonate is typically used as a solvent.

Monoethylene glycol can be commercially prepared from ethylene oxide by various known methods. These methods, although varied, all generally involve a two-stage reaction system, wherein ethylene is first converted to ethylene oxide, which is then converted to ethylene glycol. In most industrial-scale glycol production operations, the process for the production and recovery of ethylene oxide is integrated with the process for the production of ethylene glycol to maximize energy utilization and reduce costs.

In the first stage, ethylene oxide is typically produced by reacting ethylene with air or elemental oxygen in the presence of a suitable catalyst, such as a silver-based epoxidation catalyst, and often in the presence of organic moderators, such as organic halides, in an epoxidation reactor. (see Kirk Othmer's Encyclopedia of Chemical Technology, $4^{th}$ edition, Vol. 9, pages 923-940). This reaction generally occurs at pressures of 10-30 bar and temperatures of 200-300° C., and produces an epoxidation reaction product comprising ethylene oxide, unreacted reactants (such as ethylene and oxygen), various impurities (such as aldehyde impurities, including formaldehyde and acetaldehyde) and optionally other gases and/or by-products (such as nitrogen, argon, methane, ethane, water and/or carbon dioxide).

In the second stage, ethylene oxide is converted to ethylene glycol by one of several methods. In one well known method, the epoxidation reaction product from the epoxidation reactor is supplied to an ethylene oxide absorber, along with a recirculating absorbent solution, typically referred to as "lean absorbent", to absorb the ethylene oxide from the epoxidation reaction product. The ethylene oxide absorber produces an aqueous product stream comprising ethylene oxide, commonly referred to as "fat absorbent", which is then supplied to an ethylene oxide stripper, wherein steam is usually introduced counter-currently to separate the ethylene oxide as a vapor stream. The separated ethylene oxide is withdrawn at or near the top of the ethylene oxide stripper, as a more concentrated aqueous ethylene oxide stream, while an aqueous stream withdrawn from the ethylene oxide stripper as bottoms is typically recirculated to the ethylene oxide absorber for reuse as lean absorbent. The aqueous ethylene oxide stream withdrawn from the ethylene oxide stripper is then further reacted to provide ethylene glycol, either by direct hydrolysis in a hydrolysis reactor (i.e., by thermally reacting ethylene oxide with a large excess of water) or alternatively, by reacting the ethylene oxide with carbon dioxide in a carboxylation reactor in the presence of a carboxylation catalyst to produce ethylene carbonate. The ethylene carbonate may then be supplied, along with water, to a hydrolysis reactor and subjected to hydrolysis in the presence of a hydrolysis catalyst to provide ethylene glycol. Direct hydrolysis of ethylene oxide typically produces a glycol product of approximately 90-92 wt. % monoethylene glycol (MEG) (with the remainder being predominately diethylene glycol (DEG), some triethylene glycol (TEG), and a small amount of higher homologues), whereas the reaction via the ethylene carbonate intermediary typically produces a glycol product in excess of 99 wt. % MEG.

Efforts have been made to simplify the process for obtaining ethylene glycol from ethylene oxide, reducing the equipment that is required and reducing the energy consumption. For example, GB 2107712 describes a process for preparing monoethylene glycol wherein the gases from the epoxidation reactor are supplied directly to a reactor wherein ethylene oxide is converted to ethylene carbonate or to a mixture of ethylene glycol and ethylene carbonate.

Similarly, EP 0776890 describes a process wherein the gases from the epoxidation reactor are supplied to an ethylene oxide absorber, wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst, such as an iodide-containing carboxylation catalyst. The ethylene carbonate in the absorbing solution is subsequently supplied, with the addition of water, to a hydrolysis reactor and subjected to hydrolysis in the presence of a hydrolysis catalyst, such as an alkali metal hydroxide.

EP 2178815 describes a reactive absorption process for preparing monoethylene glycol, wherein the gases from the epoxidation reactor are supplied to an absorber and the ethylene oxide is contacted with lean absorbent comprising at least 20 wt. % water in the presence of one or more catalysts that promote carboxylation and hydrolysis and the majority of the ethylene oxide is converted to ethylene carbonate or ethylene glycol in the absorber.

In each of these cases, a recycle gas stream containing gases that are not absorbed by the recirculating absorbent stream will be produced from the ethylene oxide absorber. Typically, at least a portion of this recycle gas stream is treated in a carbon dioxide absorption column and then recombined with any portion of the recycle gas stream bypassing the carbon dioxide absorption column. The combined gases are then recycled to the epoxidation reactor.

However, it has been found that in those processes where the carboxylation reaction is performed in the ethylene oxide absorber using an iodide-containing carboxylation catalyst, decomposition materials and side products may be present in the recycle gas stream and/or in the fat absorbent stream. Examples of such decomposition materials and side products include gaseous iodide-containing impurities, such as alkyl iodides (e.g., methyl iodide, ethyl iodide, etc.) and vinyl iodide.

The silver-based epoxidation catalysts typically used in an epoxidation reactor are susceptible to catalyst poisoning, in particular, poisoning by gaseous iodide-containing impurities, such as alkyl iodides and vinyl iodide. Catalyst poisoning impacts the epoxidation catalyst performance, in particular the selectivity and/or the activity, and shortens the length of time the epoxidation catalyst can remain in the epoxidation reactor before it becomes necessary to exchange the catalyst with fresh catalyst. Accordingly, it is desirable to remove such catalyst poisons as much as is practicable from the recycle gas stream before it comes into contact with the epoxidation catalyst. For example, the use of a purification zone or a guard bed upstream of an epoxidation reactor is disclosed in EP 2285795, EP 2279182 and EP 2155375.

The present inventors have found that the sensitivity of epoxidation catalysts to certain gaseous iodide-containing impurities, particularly alkyl iodides and vinyl iodide, is even greater than previously expected. The present inventors have, therefore, sought to provide improved guard bed materials and improved processes to remove certain gaseous iodide-containing impurities from a recycle gas stream in the manufacture of ethylene oxide, ethylene carbonate and/or ethylene glycol.

SUMMARY

Accordingly, in one aspect, a process for producing ethylene oxide is provided, the process comprising:

contacting at least a portion of a recycle gas stream comprising an alkyl iodide impurity with a guard bed material to yield a treated recycle gas stream, wherein the guard bed material comprises a spherical support material having a diameter of less than 2 mm, and deposited on the spherical support material, silver in an amount of from 2% to 10% by weight; and contacting an epoxidation feed gas comprising ethylene, oxygen and at least a portion of the treated recycle gas stream with an epoxidation catalyst to yield an epoxidation reaction product comprising ethylene oxide.

Further, in accordance with another aspect, a process for producing ethylene carbonate and/or ethylene glycol is provided, the process comprising:

contacting at least a portion of a recycle gas stream comprising an alkyl iodide impurity with a guard bed material to yield a treated recycle gas stream, wherein the guard bed material comprises a spherical support material having a diameter of less than 2 mm, and deposited on the spherical support material, silver in an amount of from 2% to 10% by weight;

contacting an epoxidation feed gas comprising ethylene, oxygen and at least a portion of the treated recycle gas stream with an epoxidation catalyst to yield an epoxidation reaction product comprising ethylene oxide; and contacting at least a portion of the epoxidation reaction product comprising ethylene oxide with lean absorbent in the presence of an iodide-containing carboxylation catalyst to yield a fat absorbent stream comprising ethylene carbonate and/or ethylene glycol and the recycle gas stream comprising the alkyl iodide impurity.

Further, in accordance with yet another aspect, a reaction system for the production of ethylene carbonate and/or ethylene glycol is provided, the reaction system comprising:

a recycle gas loop fluidly connected to a source of ethylene and oxygen;

an epoxidation reactor comprising an epoxidation catalyst, an inlet, and an outlet, wherein the inlet of the epoxidation reactor is fluidly connected to the recycle gas loop;

an ethylene oxide absorber comprising an iodide-containing carboxylation catalyst, an inlet, and an outlet, wherein the outlet of the epoxidation reactor is fluidly connected to the inlet of the ethylene oxide absorber, the outlet of the ethylene oxide absorber is fluidly connected to the recycle gas loop, and the ethylene oxide absorber is configured to produce a recycle gas stream comprising an alkyl iodide impurity and a fat absorbent stream comprising ethylene carbonate and/or ethylene glycol; and a guard bed system comprising an inlet, an outlet, and one or more guard bed vessels comprising a guard bed material, wherein the guard bed material comprises a spherical support material having a diameter of less than 2 mm, and deposited on the spherical support material, silver in an amount of from 2% to 10% by weight, wherein the inlet and the outlet of the guard bed system is fluidly connected to the recycle gas loop, and the guard bed material is configured to remove at least a portion of the alkyl iodide impurity from at least a portion of the recycle gas stream.

BRIEF DESCRIPTION OF THE DRAWINGS

Some specific example embodiments of the disclosure may be understood by referring, in part, to the following description and the accompanying drawings.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION

It has been found that when ethylene oxide is catalytically reacted in the ethylene oxide absorber in the presence of an iodide-containing carboxylation catalyst, then gaseous iodide-containing impurities may be formed which exit the ethylene oxide absorber with the recycle gas stream. These gaseous iodide-containing impurities, particularly alkyl iodides and vinyl iodide, can poison the epoxidation catalyst in the epoxidation reactor, even in minute quantities.

Treating the recycle gas stream by contacting the stream with a guard bed material capable of at least partially absorbing such iodide-containing impurities can reduce the amount of such impurities in the recycle gas stream and thus protect the performance of the epoxidation catalyst, in particular the selectivity and/or activity of the catalyst, as well as the duration of time the epoxidation catalyst can remain in the epoxidation reactor before it becomes necessary to exchange the catalyst with fresh epoxidation catalyst.

Accordingly, described herein are processes and associated systems for producing ethylene oxide, ethylene carbonate and/or ethylene glycol wherein a recycle gas stream comprising an alkyl iodide impurity, such as methyl iodide, ethyl iodide, or a combination thereof, is contacted with a guard bed material that comprises a spherical support material having a diameter of less than 2 mm, and deposited on the spherical support material, silver in an amount of from 2% to 10% by weight to reduce the amount of the alkyl iodide impurity present in the recycle gas stream.

By using the processes and systems disclosed herein, the amount of an alkyl iodide impurity, such as methyl iodide and/or ethyl iodide, present in a recycle gas stream is reduced to the very low levels the present inventors have now found to be required for the performance of the epoxidation catalyst to remain substantially unaffected by its presence. In particular, the amount of alkyl iodide present in a treated recycle gas stream is preferably no more than 6 ppbv, preferably no more than 5 ppbv, more preferably no more than 3 ppbv, even more preferably no more than 2 ppbv, most preferably no more than 1 ppbv. Similarly, the amount of alkyl iodide present in the epoxidation feed gas supplied to the epoxidation reactor is preferably no more than 6 ppbv, preferably no more than 5 ppbv, more preferably no more than 3 ppbv, even more preferably no more than 2 ppbv, most preferably no more than 1 ppbv.

Figure 1:
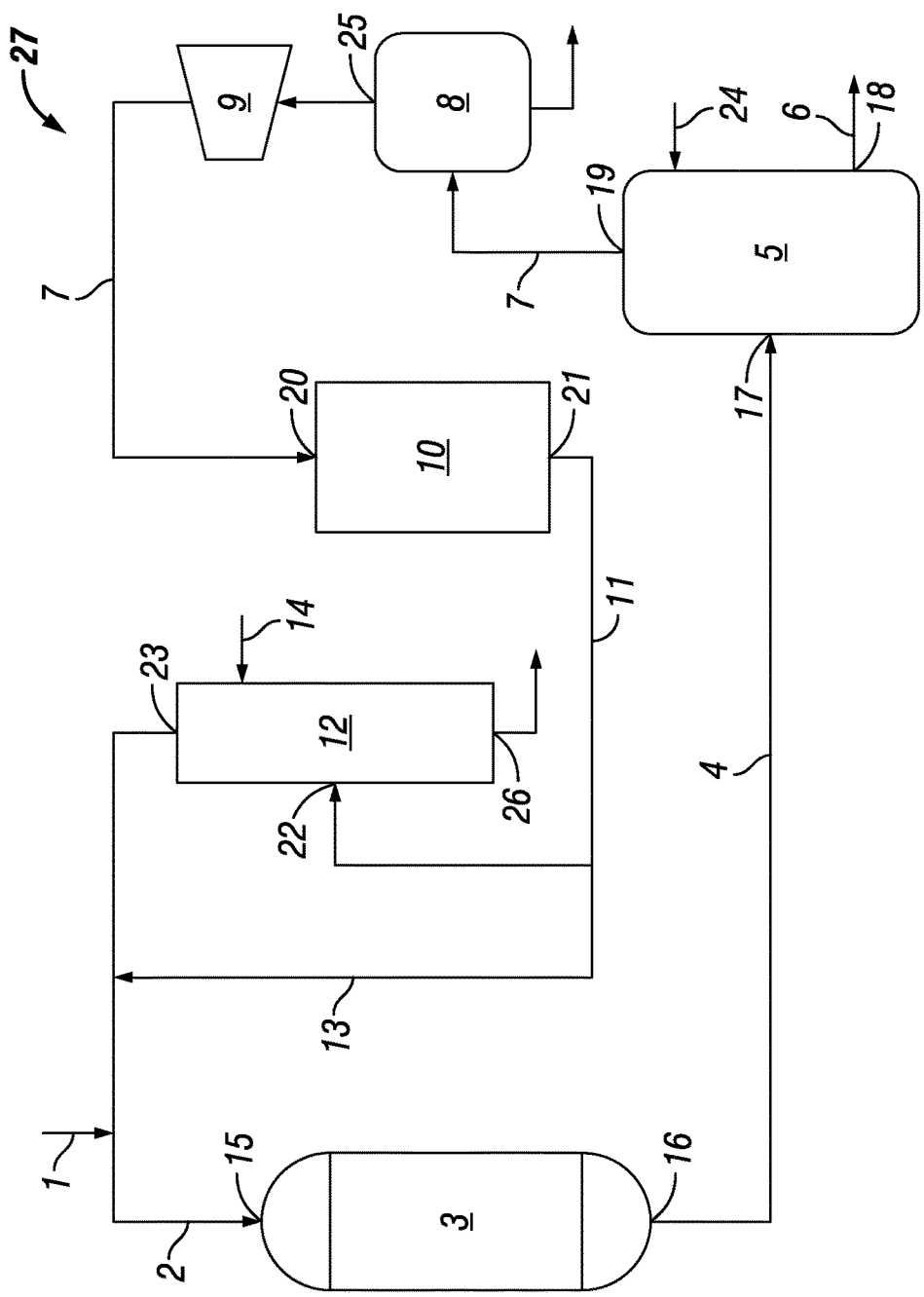
FIGS. 1-4 are schematic illustrations showing exemplary embodiments of the present disclosure.

Reference is made to FIG. 1, which is a schematic view of a reaction system (27) for the production of ethylene carbonate and/or ethylene glycol, according to an embodiment of the present disclosure. Reaction system (27) generally comprises epoxidation reactor (3), ethylene oxide absorber (5), guard bed system (10) and carbon dioxide absorber (12). It will be clear to the skilled person, that as schematic diagrams these figures do not show all necessary inputs, outputs, recycle streams, etc. that may be present in the reaction system. Furthermore, in the figures herein, as will be appreciated, elements can be added, exchanged, and/or eliminated so as to provide any number of additional embodiments and the sequence in which various feed components are introduced into the process and their respective points of introduction, as well as the flow connections, may be varied from that depicted. In addition, as will be appreciated, the proportion and the relative scale of the elements provided in the figure are intended to illustrate the embodiments of the present disclosure, and should not be taken in a limiting sense.

As shown in FIG. 1, epoxidation feed gas (2) is supplied to epoxidation reactor (3) via an inlet, such as inlet (15), which is in fluid communication with the recycle gas loop. Components of epoxidation feed gas (2) include at least a portion of treated recycle gas stream (11) and typically further comprise ethylene, oxygen, ballast gas (e.g., methane or nitrogen), and a reaction modifier (e.g., monochloroethane, vinyl chloride or dichloroethane), which may be supplied to the recycle gas loop via one or more inlets, such as inlet (1).

In epoxidation reactor (3), ethylene is reacted with oxygen in the presence of an epoxidation catalyst to yield epoxidation reaction product stream (4), which typically comprises ethylene oxide, unreacted ethylene and oxygen, reaction modifier, ballast gas, various by-products of the epoxidation reaction (e.g., carbon dioxide and water) and various impurities. Epoxidation reaction product stream (4) exits epoxidation reactor (3) via an outlet, such as outlet (16), which is in fluid communication with an inlet of ethylene oxide absorber (5), such as inlet (17). Preferably, epoxidation reaction product stream (4) is cooled in one or more coolers (not shown), preferably with generation of steam at one or more temperature levels before being supplied to ethylene oxide absorber (5).

Epoxidation reaction product stream (4) and lean absorbent stream (24) are supplied to ethylene oxide absorber (5). In ethylene oxide absorber (5), the epoxidation reaction product is brought into intimate contact with the lean absorbent in the presence of an iodide-containing carboxylation catalyst, and more preferably in the presence of an iodide-containing carboxylation catalyst and a hydrolysis catalyst. At least a portion of, and preferably substantially all of, the ethylene oxide in the epoxidation reaction product is absorbed into the lean absorbent. Fat absorbent stream (6), which comprises ethylene carbonate and/or ethylene glycol, is withdrawn from ethylene oxide absorber (5) via an outlet, such as outlet (18) and may optionally be supplied to one or more finishing reactors (not shown).

Any gases not absorbed in ethylene oxide absorber (5) are withdrawn at or near the top of ethylene oxide absorber (5) as recycle gas stream (7) via an outlet, such as outlet (19), which is in fluid communication with the recycle gas loop. The recycle gas loop comprises interconnecting pipework between outlet (19) of ethylene oxide absorber (5) and inlet (15) of epoxidation reactor (3) and optionally may further comprise heat exchanger(s), a vapor-liquid separator, such as vapor-liquid separator (8) (e.g., knock-out vessel, flash vessel, etc.), a recycle gas compressor, such as recycle gas compressor (9), and/or a carbon dioxide absorber, such as carbon dioxide absorber (12).

Recycle gas stream (7) comprises an alkyl iodide impurity, such as methyl iodide, ethyl iodide, or a combination thereof, due to the presence of the iodide-containing carboxylation catalyst in ethylene oxide absorber (5) and the reaction conditions therein. Optionally, the recycle gas stream may further comprise a vinyl iodide impurity. Typically, recycle gas stream (7) further comprises one or more of ethylene, oxygen, reaction modifier, ballast gas, carbon dioxide and water. To reduce the amount of the alkyl iodide impurity, recycle gas stream (7) is supplied to guard bed system (10) via an inlet, such as inlet (20) that is in fluid communication with the recycle gas loop.

In guard bed system (10), recycle gas stream (7) is brought into contact with a packed bed of guard bed material in a guard bed vessel. The guard bed material comprises a spherical support material having a diameter of less than 2 mm, and deposited on the spherical support material, silver in an amount of from 2% to 10% by weight. By contacting recycle gas stream (7) with the guard bed material, at least a portion of the alkyl iodide impurity is removed from recycle gas stream (7) to yield treated recycle gas stream (11), which comprises a reduced amount of the alkyl iodide impurity relative to recycle gas stream (7). Treated recycle gas stream (11) exits guard bed system (10) via an outlet, such as outlet (21), which is in fluid communication with the recycle gas loop.

Figure 3:
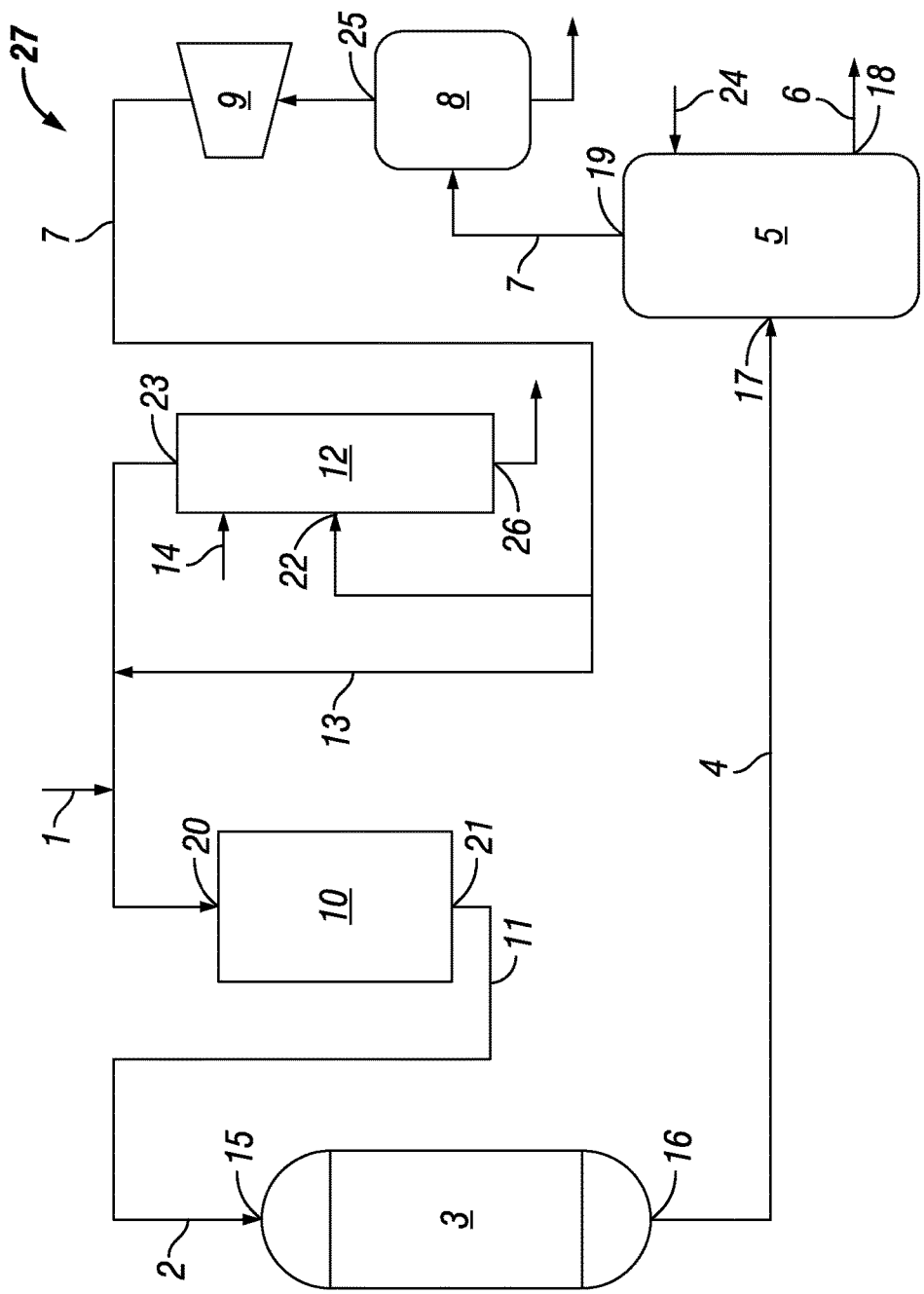

Suitably, guard bed system (10) may be located anywhere in the recycle gas loop. For example, as shown in FIG. 1, guard bed system (10) may preferably be located in the recycle gas loop between outlet (19) of ethylene oxide absorber (5) and an inlet of carbon dioxide absorber (12), such as inlet (22), and more preferably between an outlet of recycle gas compressor (9) and inlet (22) of carbon dioxide absorber (12). Also, as shown in FIG. 1, guard bed system (10) may preferably be located in the recycle gas loop between an outlet of vapor-liquid separator (8), such as outlet (25), and inlet (15) of epoxidation reactor (3), and more preferably between outlet (25) of vapor-liquid separator (8) and inlet (22) of carbon dioxide absorber (12). Further, as shown in FIG. 1, guard bed system (10) may preferably be located in the recycle gas loop upstream from inlet (1), where additional component(s) of epoxidation feed gas (2), such as ethylene, oxygen, ballast gas and/or a reaction modifier, may be supplied to the recycle gas loop, or alternatively, downstream from such a point, as shown in FIG. 3, for example.

Preferably, as shown in FIG. 1, at least a portion of treated recycle gas stream (11) is supplied to carbon dioxide absorber (12) via an inlet, such as inlet (22), along with recirculating absorbent stream (14). In carbon dioxide absorber (12), the treated recycle gas stream is brought into contact with recirculating absorbent stream (14). At least a portion of the carbon dioxide in the treated recycle gas stream is absorbed into the recirculating absorbent stream and is withdrawn from carbon dioxide absorber (12) via an outlet, such as outlet (26). The portion of the treated recycle gas stream that was supplied to carbon dioxide absorber (12), but that was not absorbed by the recirculating absorbent stream exits via an outlet, such as outlet (23), and is preferably re-combined with any portion of the treated recycle gas stream that bypassed carbon dioxide absorber (12) via bypass (13). The treated recycle gas stream is then recycled to inlet (15) of epoxidation reactor (3) as a component of epoxidation feed gas (2).

Optionally, one or more heating or cooling devices, such as a heat exchanger, may be present in the recycle gas loop in order to alter the temperature of recycle gas stream (7) (e.g., so as to provide recycle gas stream (7) to guard bed system (10) at an optimal temperature) and/or in order to alter the temperature of treated recycle gas stream (11) (e.g., so as to provide treated recycle gas stream (11) to epoxidation reactor (3)) or for any further treatment of the treated recycle gas stream prior to being provided to epoxidation reactor (3).

Figure 2:
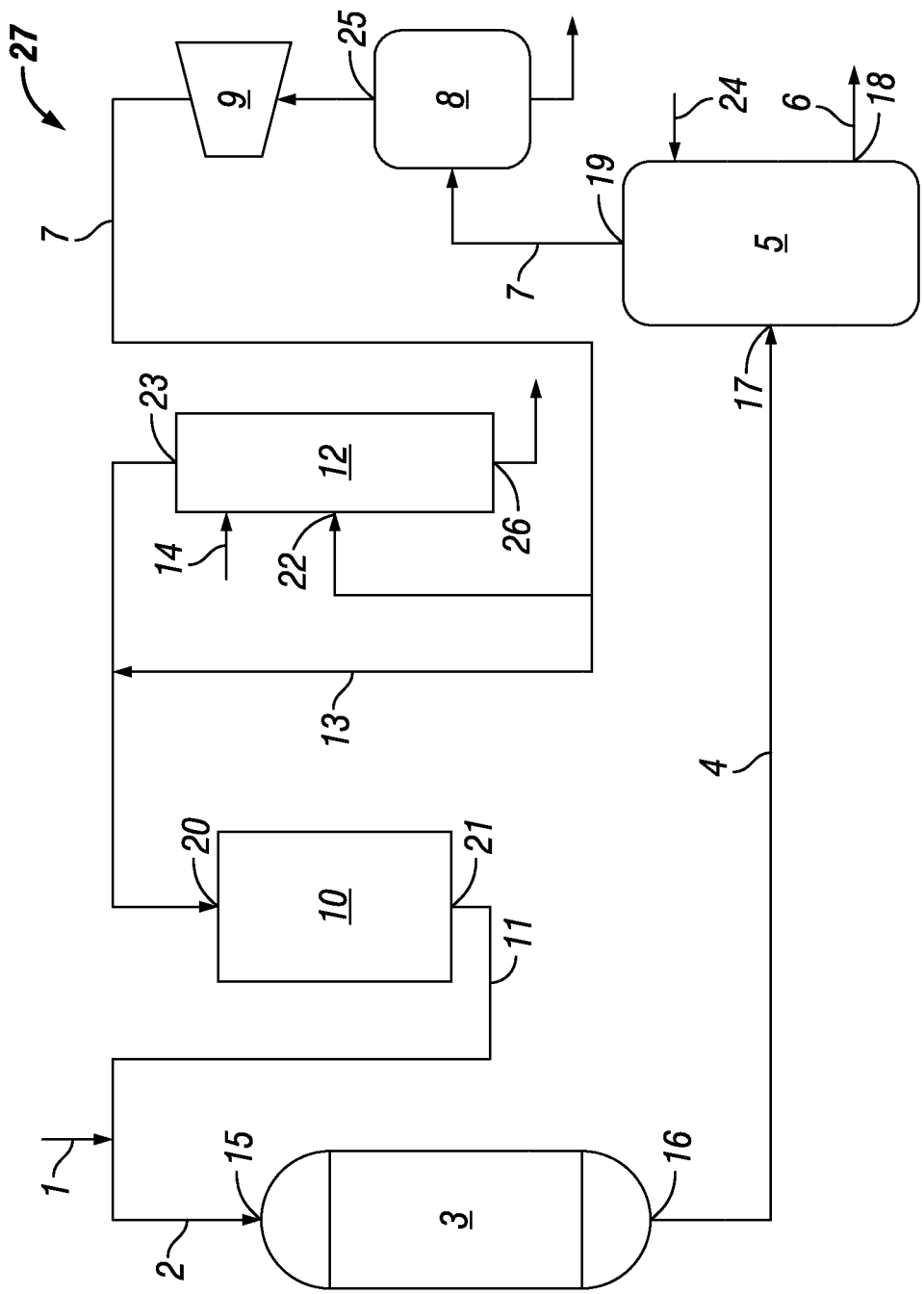

FIG. 2 is a schematic view of a reaction system (27) for the production of ethylene carbonate and/or ethylene glycol, similar to FIG. 1 except that guard bed system (10) is positioned in the recycle gas loop downstream from carbon dioxide absorber (12). As shown in FIG. 2, at least a portion of recycle gas stream (7) is supplied to inlet (22) of carbon dioxide absorber (12), while the remaining portion of recycle gas stream (7) (if any) bypasses carbon dioxide absorber (12) via bypass (13). The portion of the recycle gas stream that was supplied to carbon dioxide absorber (12), but that was not absorbed by the recirculating absorbent stream exits via outlet (23), and is preferably re-combined with any portion of the recycle gas stream that bypassed carbon dioxide absorber (12) via bypass (13) and is supplied to inlet (20) of guard bed system (10). Treated recycle gas stream (11) exits guard bed system (10) via outlet (21), which is in fluid communication with the recycle gas loop, and is recycled to inlet (15) of epoxidation reactor (3) as a component of epoxidation feed gas (2).

FIG. 3 is a schematic view of a reaction system (27) for the production of ethylene carbonate and/or ethylene glycol, similar to FIG. 2 except that guard bed system (10) is positioned in the recycle gas loop downstream from inlet (1), where one or more additional components of epoxidation feed gas (2), such as ethylene, oxygen, ballast gas and/or a reaction modifier, may be supplied to the recycle gas loop.

Figure 4:
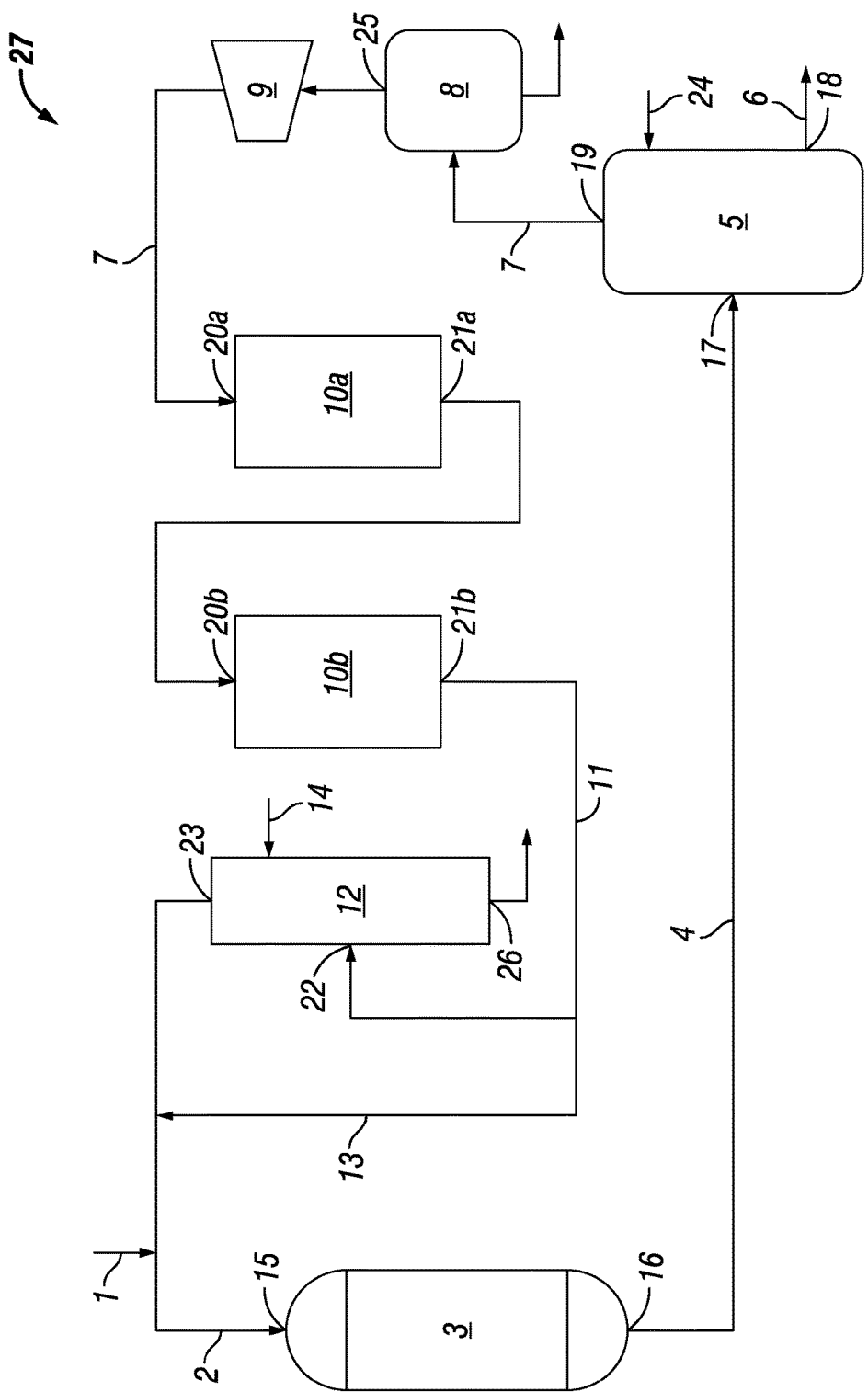

FIG. 4 is a schematic view of a reaction system (27) for the production of ethylene carbonate and/or ethylene glycol, similar to FIG. 1 except that the guard bed system comprises a plurality of guard bed vessels. As shown in FIG. 4, recycle gas stream (7) is supplied via inlet (20*a*) to a guard bed system comprising two guard bed vessels (10*a*) and (10*b*) that each comprise a packed bed of guard bed material. The gas stream exiting guard bed vessel (10*a*) via outlet (21*a*) is subsequently supplied to guard bed vessel (10*b*) via inlet (20*b*). Treated recycle gas stream (11) exits the guard bed system via outlet (21*b*), which is in fluid communication with the recycle gas loop. Preferably, at least a portion of treated recycle gas stream (11) is supplied to carbon dioxide absorber (12) before it is recycled to inlet (15) of epoxidation reactor (3) as a component of epoxidation feed gas (2).

A guard bed system of the present disclosure comprises an inlet, an outlet and one or more guard bed vessels comprising a guard bed material. Suitably, the inlet of the guard bed system is fluidly connected to the recycle gas loop so that at least a portion of a recycle gas stream from the ethylene oxide absorber is supplied (either directly or indirectly) to the guard bed system. Within the guard bed system, the recycle gas stream passes through the one or more guard bed vessels and contacts a guard bed material whereby alkyl iodide impurities are removed. A treated recycle gas stream is removed from an outlet of the guard bed system. Said treated recycle gas stream will contain a reduced amount of alkyl iodide as compared to the recycle gas stream. Suitably, the outlet of the guard bed system is fluidly connected to the recycle gas loop so that at least a portion of a treated recycle gas stream from the guard bed system is supplied (either directly or indirectly) to an inlet of the epoxidation reactor.

Preferably, a guard bed system comprises two or more guard bed vessels. Optionally, the guard bed system comprises more than two, for example three or four, guard bed vessels. When two or more guard bed vessels are present in the guard bed system, the guard bed vessels may be arranged in parallel with associated switching means to allow the process to be switched between the vessels, thus maintaining a continuous operation of the process. Alternatively, the guard bed vessels within the guard bed system may be arranged in series or in series in sequential order, with associated valves, as described in co-pending application EP15200254.9, which is incorporated by reference herein.

A guard bed vessel suitable for use in the present disclosure includes any vessel in which a bed of guard bed material can be held and through which a recycle gas stream can be passed such that the recycle gas stream comes into contact with the guard bed material. Preferably, the guard bed vessel is a fixed bed reactor, such as an axial fixed bed reactor, wherein the recycle gas stream is contacted with the guard bed material as an axial flow; or a radial flow fixed bed reactor, wherein the recycle gas stream is supplied from an inlet to the outside of the fixed bed and passes through the fixed bed to the center of the guard bed vessel and then to an outlet. A radial flow fixed bed reactor is particularly preferred because it will generally produce less of a pressure drop across the bed of guard bed material. Other suitable types of guard bed vessels will be apparent to those of ordinary skill in the art and are to be considered within the scope of the present disclosure.

Without wishing to be bound by any particular theory, it is believed that by contacting a recycle gas stream comprising an alkyl iodide impurity with a guard bed material of the present disclosure, at least a portion of the alkyl iodide impurity present in the recycle gas stream is removed by chemical or physical means including, but not limited to, reaction with the impurity and absorption of the impurity.

The operating conditions within the one or more guard bed vessels in the guard bed system can be adjusted according to overall processing conditions. In general, the pressure in the one or more guard bed vessels in the guard bed system is determined by the pressure of the recycle gas loop. Preferably, the operating pressure can range from 1 to 4 MPa (gauge), more preferably from 2 to 3 MPa (gauge). Additionally, a guard bed vessel in the guard bed system is generally operated at an elevated temperature (relative to ambient).

Preferably, the one or more guard bed vessels in the guard bed system are operated at a temperature of at least 80° C., more preferably at least 100° C., even more preferably at least at least 115° C., most preferably at least 120° C. Further, the one or more guard bed vessels in the guard bed system are preferably operated at a temperature of at most 145° C., more preferably at most 140° C., most preferably at most 135° C., or from 100° C. to 145° C., or from 115° C. to 140° C., or from 120° C. to 135° C.

Optionally, a guard bed system may be preceded or followed by a further guard bed device. Such a guard bed device may be of a standard set up known in the art, such as a simple, single bed, guard bed vessel or two such guard beds arranged in parallel or in series to allow the feed to be switched between the two.

The one or more guard bed vessels each comprise a bed of guard bed material. It is preferred that all guard bed vessels within the guard bed system contain the same guard bed material. Suitable bed dimensions of a bed of guard bed material may readily be determined using known engineering principles. Preferably, a guard bed vessel comprises a guard bed material present in a bed that is sized to provide a contact time of the guard bed material with the incoming recycle gas stream that is sufficient to provide the desired degree of removal of the alkyl iodide impurity from the recycle gas stream.

In accordance with the present disclosure, one or more guard bed vessels in a guard bed system comprise a guard bed material that comprises a spherical support material having a diameter of less than 2 mm, and deposited on the spherical support material, silver in an amount of from 2% to 10% by weight. As used herein, the term "spherical support material" refers to a support material that, when observed under a scanning electron microscope, has a major axis to minor axis ratio of 1.0 to 1.25. Suitably, a spherical support material may have a diameter of less than 2 mm, or 1.8 mm or less, or 1.6 mm or less, or 1.5 mm or less, or 1.3 mm or less, or 1.0 mm or less, or a diameter from 0.25 mm to less than 2 mm, or from 0.5 mm to less than 2 mm, or from 0.75 mm to less than 2 mm, or from 1 mm to less than 2 mm, or from 0.25 mm to 1.5 mm, or from 0.5 mm to 1.5 mm, or from 0.75 mm to 1.5 mm, or from 1 mm to 1.5 mm.

Suitably, the spherical support material may comprise alumina, titania, zirconia, silica, activated carbon, or any combination thereof. Preferably, the spherical support material comprises alumina, in particular gamma-alumina. A suitable spherical support material may have a surface area of more than 20 $m^2/g$, relative to the weight of the spherical support material, or at least 25 $m^2/g$, or at least 50 $m^2/g$, or at least 75 $m^2/g$, or at least 100 $m^2/g$, or at least 125 $m^2/g$, or at most 1200 $m^2/g$, or at most 500 $m^2/g$, or at most 300 $m^2/g$, or at most 200 $m^2/g$, or at most 175 $m^2/g$, or from 20 $m^2/g$ to 1200 $m^2/g$, or from 50 $m^2/g$ to 500 $m^2/g$, or from 75 $m^2/g$ to 300 $m^2/g$, or from 100 $m^2/g$ to 200 $m^2/g$, or from 125 $m^2/g$ to 175 $m^2/g$, on the same basis. As used herein, "surface area" is understood to refer to the surface area of the spherical support material as measured in accordance with the B.E.T. (Brunauer, Emmett and Teller) method as described in detail in Brunauer, S., Emmet, P. Y. and Teller, E., J. Am. Chem. Soc., 60, 309-16 (1938).

The guard bed material further comprises silver, which is deposited on the spherical support material, in an amount of at least 2% by weight and no more than 10% by weight, calculated as the amount of silver relative to the total weight of the guard bed material. Preferably, the guard bed material comprises silver in an amount of from 2% to 10% by weight, or from 2% to 9% by weight, or from 2% to 8% by weight, or from 2% to 7% by weight, or from 2% to 6% by weight, or from 3% to 9%, or from 3% to 8%, or from 3% to 7%, or from 3% to 6%, or from 4% to 8% by weight, or from 4.5% to 7% by weight, or at most 8% by weight, or at most 7% by weight, or at most 6% by weight, on the same basis. Although it is possible for a guard bed material to comprise silver in an amount in excess of 10% by weight, it is preferred to employ silver in an amount of 10% by weight or less, as little to no benefit is derived from the further addition of silver.

Optionally, the guard bed material further comprises at least one of an alkali metal, an alkaline earth metal, or a combination thereof. Preferably, the alkali metal may be selected from sodium, potassium, lithium, rubidium, cesium, and combinations thereof, in particular sodium and potassium. Preferably, the alkaline earth metal may be selected from calcium, magnesium, strontium, barium, and combinations thereof. The specific form in which an alkali and/or alkaline earth metal is provided is not limited, and may include any of the wide variety of forms known. For example, the alkali and/or alkaline earth metal may suitably be provided as an ion (e.g., cation), or as a compound (e.g., alkali metal salts, alkaline earth metal salts, etc.). Generally, suitable compounds are those which can be solubilized in an appropriate solvent, such as a water-containing solvent. Without wishing to be bound by theory, it is believed that the alkali or alkaline earth metals reduce the amount of acidic sites present on the surface of the spherical support material which can react with a hydrocarbon, such as ethylene, forming unwanted by-products.

As will be appreciated by those of skill in the art, while a specific form of an alkali and/or alkaline earth metal may be provided during preparation of the guard bed material, it is possible that during the conditions of preparation of the guard bed material and/or during use, the particular form initially present may be converted to another form. Indeed, once deposited on the spherical support material and/or during use of the guard bed material, the specific form of the alkali and/or alkaline earth metal may not be known. Furthermore, in many instances, analytical techniques may not be sufficient to precisely identify the form that is present. Accordingly, the present disclosure is not intended to be limited by the exact form of the alkali and/or alkaline earth metal that may ultimately exist on the guard bed material during use. Additionally, it should be understood that while a particular compound may be used during preparation (e.g., potassium hydroxide is added to an impregnation solution), it is possible that the counter ion added during preparation of the guard bed material may not be present in the finished guard bed material (e.g., a guard bed material made using an impregnation solution comprising potassium hydroxide may be analyzed to contain potassium but not hydroxide in the finished guard bed material).

When included, an alkali metal, an alkaline earth metal or a combination thereof may be deposited on the spherical support material in an amount of at least 0.1% by weight and no more than 5% by weight, calculated as the amount of the element relative to the total weight of the guard bed material. Preferably, the guard bed material comprises an alkali metal, an alkaline earth metal or a combination thereof in an amount of from 0.1% to 5% by weight, or from 0.2% to 4% by weight, or from 0.3% to 3% by weight, or from 0.4% to 2% by weight, or from 0.5% to 1% by weight or at least 0.1% by weight, or at least 0.2% by weight, or at least 0.3% by weight, or at least 0.4% by weight, or at least 0.5% by weight, or at most 5%, or at most 4%, or at most 3%, or at most 2%, on the same basis. For purposes of convenience, the amount of the alkali or alkaline earth metal deposited on a spherical support material is measured as the element, irrespective of the form in which it is present. Although it is possible for a guard bed material to comprise an alkali metal, an alkaline earth metal or a combination thereof in an amount in excess of 5% by weight, it is preferred to employ an alkali metal, an alkaline earth metal or a combination thereof in an amount of 5% by weight or less, as little to no benefit is derived from the further addition of an alkali metal, an alkaline earth metal or a combination thereof.

It should be understood that the amount of alkali and/or alkaline earth metal deposited on the spherical support material is not necessarily the total amount of alkali and/or alkaline earth metal present in the guard bed material. Rather, the amount deposited reflects the amount that has been added to the spherical support material (e.g., via impregnation). As such, the amount of alkali and/or alkaline earth metal deposited on the spherical support material does not include any amount of alkali and/or alkaline earth metals that may be locked into the spherical support material, for example, by calcining, or are not extractable in a suitable solvent, such as water or lower alkanol or amine or mixtures thereof. It is also understood that the source of the alkali and/or alkaline earth metal may be the spherical support material itself. That is, the spherical support material may contain extractable amounts of an alkali and/or alkaline earth metal that can be extracted with a suitable solvent, such as water or lower alkanol, thus preparing a solution from which the alkali and/or alkaline earth metal may be deposited or redeposited on the spherical support material.

Well known methods can be employed to analyze for the amounts of silver, and alkali and/or alkaline earth metal deposited onto the spherical support material. The skilled artisan may employ, for example, material balances to determine the amounts of any of these deposited components. As an example, if the spherical support material is weighed prior to and after deposition of silver and an alkali or alkaline earth metal, then the difference in the two weights will be equal to the amount of silver and the alkali or alkaline earth metal deposited onto the spherical support material, from which the amount of the deposited alkali and/or alkaline earth metal can be calculated. Additionally, the amount of the deposited silver and alkali and/or alkaline earth metal can be calculated based upon the ratio of the concentration of silver and alkali or alkaline earth metal included in the impregnation solution(s) and the total weight in the finished guard bed material.

Alternatively, the amount of an alkali and/or alkaline earth metal deposited on the spherical support material may also be determined by known leaching methods, wherein the amount of metallic leachables present in the spherical support material and the amount of metallic leachables present in the guard bed material are independently determined and the difference between the two measurements reflect the total amount of alkali or alkaline earth metal deposited on the spherical support material. As an example, the amount of an alkali metal deposited on a spherical support material may be determined by separately leaching a 10-gram sample of the spherical support material and a 10-gram sample of the guard bed material with 100 mL of 10% w nitric acid for 30 minutes at 100° C. (1 atm) and determining the amount of the alkali metal present in the extracts using standard Atomic Absorption spectroscopy techniques. The difference in the measurements between the spherical support material and the guard bed material reflect the amount of the alkali metal deposited onto the spherical support material.

The specific manner in which a guard bed material is prepared is generally not limited, and therefore any known preparative method may be used, provided that the silver and optionally, the alkali and/or alkaline earth metal are deposited on the spherical support material in a suitable manner. In general, a guard bed material may be prepared by contacting (e.g., impregnating) a spherical support material with one or more solutions comprising silver and optionally, at least one of an alkali metal, an alkaline earth metal, or a combination thereof; and subsequently depositing silver and the alkali and/or alkaline metal (if present) on the spherical support material, typically by heating the impregnated spherical support material. For further description of impregnation methods, reference may be made to U.S. Pat. Nos. 4,761,394, 4,766,105, 5,380,697, 5,739,075, 6,368,998 and 6,656,874, which are incorporated herein by reference.

Processes of the present disclosure further comprise contacting an epoxidation feed gas comprising ethylene, oxygen and at least a portion of the treated recycle gas stream with an epoxidation catalyst to yield an epoxidation reaction product comprising ethylene oxide. Although an epoxidation process may be carried out in a variety of known ways, it is preferred to carry out the epoxidation process as a continuous, gas-phase process, wherein an epoxidation feed gas is contacted with an epoxidation catalyst in the gas phase in an epoxidation reactor. The following description provides further details of the epoxidation catalyst, epoxidation reactor, epoxidation feed gas and the epoxidation process.

Suitable epoxidation catalysts that may be employed are known in the art and generally comprise a carrier, and deposited on the carrier, silver and optionally, one or more promoters, such a rhenium promoter, an alkali metal promoter, etc. Detailed preparative techniques for carriers and epoxidation catalysts are generally known in the art. For additional disclosure regarding suitable epoxidation catalysts and preparative techniques, reference may be made to, for example U.S. Pat. Nos. 4,761,394, 8,921,586 and 8,932,979 and U.S. Patent Publication Nos. 20080281118 and 20110034710, which are incorporated herein by reference.

An epoxidation reactor suitable for use in the systems and processes of the present disclosure may be any reactor vessel used to react ethylene and oxygen in the presence of an epoxidation catalyst, and comprises an inlet that is in fluid communication to the recycle gas loop and further comprises an outlet that is in fluid communication with an inlet of an ethylene oxide absorber. Suitable epoxidation reactors may include any of a wide variety of known reactor vessels, such as a fixed bed reactor (e.g., a fixed bed tubular reactor), a continuous stirred tank reactor (CSTR), a fluid bed reactor, etc. Additionally, a plurality of epoxidation reactors may be used in parallel. One commercial example of a suitable epoxidation reactor is a shell-and-tube heat exchanger comprising a plurality of reactor tubes, wherein the shell contains a coolant to regulate the temperature of the epoxidation reactor and wherein the plurality of tubes are parallel, elongated tubes that contain the epoxidation catalyst.

In accordance with the present disclosure, an epoxidation feed gas comprises ethylene, oxygen and a treated recycle gas stream. Optionally, the epoxidation feed gas may further comprise carbon dioxide, a ballast gas, a reaction modifier, and a combination thereof. As used herein, the term "epoxidation feed gas" refers to the totality of the gas stream supplied at the inlet of the epoxidation reactor, which may suitably be comprised of a combination of one or more gas stream(s), such as an ethylene stream, an oxygen stream, a treated recycle gas stream, etc. Further, it should be understood that the concentrations discussed below of individual feed components in the epoxidation feed gas reflect the total concentration of that component in the epoxidation feed gas, irrespective of the source(s).

Ethylene may be present in the epoxidation feed gas in a concentration that may vary over a wide range. However, ethylene is typically present in the epoxidation feed gas in a concentration of at least 5 mole-%, relative to the total epoxidation feed gas, or at least 8 mole-%, or at least 10 mole-%, or at least 12 mole-%, or at least 14 mole-%, or at least 20 mole-%, or at least 25 mole-%, on the same basis. Similarly, ethylene is typically present in the epoxidation feed gas in a concentration of at most 65 mole-%, or at most 60 mole-%, or at most 55 mole-%, or at most 50 mole-%, or at most 48 mole-%, on the same basis. In some embodiments, ethylene may be present in the epoxidation feed gas in a concentration of from 5 mole-% to 60 mole-%, relative to the total epoxidation feed gas, or from 10 mole-% to 50 mole-%, or from 12 mole-% to 48 mole-%, on the same basis.

In addition to ethylene, the epoxidation feed gas further comprises oxygen, which may be provided either as pure oxygen or air. See W. E. Evans, J. M. Kobe, M. F. Lemanski and R. L. June, "Industrial Epoxidation Processes", Encyclopedia of Catalysis (Wiley-Interscience), Volume 3, page 246 (2003). In an air-based process, air or air enriched with oxygen is employed, while in an oxygen-based process, high-purity (at least 95 mole-%) oxygen or very high purity (at least 99.5 mole-%) oxygen is employed. Reference may be made to U.S. Pat. No. 6,040,467, incorporated by reference herein, for further description of oxygen-based epoxidation processes. Presently, most epoxidation plants are oxygen-based, which is preferred. Typically, in oxygen-based processes, the epoxidation feed gas further comprises a ballast gas, which will be discussed in more detail below, to maintain the oxygen concentration below the maximum level allowed by flammability considerations.

In general, the oxygen concentration in the epoxidation feed gas should be less than the concentration of oxygen that would form a flammable mixture at either the inlet or the outlet of the epoxidation reactor at the prevailing operating conditions. Often, in practice, the oxygen concentration in the epoxidation feed gas may be no greater than a predefined percentage (e.g., 95%, 90%, etc.) of oxygen that would form a flammable mixture at either the inlet or the outlet of the epoxidation reactor at the prevailing operating conditions. Although the oxygen concentration may vary over a wide range, the oxygen concentration in the epoxidation feed gas is typically at least 0.5 mole-%, relative to the total epoxidation feed gas, or at least 1 mole-%, or at least 2 mole-%, or at least 3 mole-%, or at least 4 mole-%, or at least 5 mole-%, on the same basis. Similarly, the oxygen concentration of the epoxidation feed gas is typically at most 20 mole-%, relative to the total epoxidation feed gas, or at most 15 mole-%, or at most 12 mole-%, or at most 10 mole-%, on the same basis. In some embodiments, oxygen may be present in the epoxidation feed gas in a concentration of from 1 mole-% to 15 mole-%, relative to the total epoxidation feed gas, or from 2 mole-% to 12 mole-%, or from 3 mole-% to 10 mole-%, on the same basis. Typically, as the oxygen concentration in the epoxidation feed gas increases, the required operating temperature decreases. However as previously mentioned, in practice, flammability is generally the limiting factor for the maximum concentration of oxygen in the epoxidation feed gas. Accordingly, in order to remain outside the flammable regime, the oxygen concentration of the epoxidation feed gas may be lowered as the ethylene concentration of the epoxidation feed gas is increased. It is within the ability of one skilled in the art to determine a suitable concentration of oxygen to be included in the epoxidation feed gas, taking into consideration, for example, the overall epoxidation feed gas composition, along with the other operating conditions, such as pressure and temperature.

Optionally, the epoxidation feed gas may further comprise carbon dioxide. When present, carbon dioxide is typically present in the epoxidation feed gas in a concentration of 0.10 mole-% or greater, relative to the total epoxidation feed gas, or 0.12 mole-% or greater, or 0.15 mole-% or greater, or 0.17 mole-% or greater, or 0.20 mole-% or greater, or 0.22 mole-% or greater, or 0.25 mole-% or greater, on the same basis. Similarly, carbon dioxide is generally present in the epoxidation feed gas in a concentration of at most 10 mole-%, relative to the total epoxidation feed gas, or at most 8 mole-%, or at most 5 mole-%, or at most 3 mole-%, or at most 2.5 mole-%, on the same basis. In some embodiments, carbon dioxide may be present in the epoxidation feed gas in a concentration of from 0.10 mole-% to 10 mole-%, relative to the total epoxidation feed gas, or from 0.15 mole-% to 5 mole-%, or from 0.20 mole-% to 3 mole-%, or from 0.25 mole-% to 2.5 mole-%, on the same basis. Carbon dioxide is produced as a by-product of the epoxidation reaction and is typically introduced into the epoxidation feed gas as a component of the treated recycle gas stream. Carbon dioxide generally has an adverse effect on catalyst performance, with the operating temperature increasing as the concentration of carbon dioxide present in the epoxidation feed gas increases. Accordingly, in the commercial production of ethylene oxide, it is common for at least a portion of the carbon dioxide to be continuously removed (e.g., via a carbon dioxide absorber) to maintain the concentration of carbon dioxide in the epoxidation feed gas at an acceptable level.

The epoxidation feed gas optionally may further comprise a ballast gas, such as nitrogen, methane, or a combination thereof. When used, a ballast gas may be added to the epoxidation feed gas to increase the oxygen flammability concentration. If desired, a ballast gas may be present in the epoxidation feed gas in a concentration of at least 5 mole-%, relative to the total epoxidation feed gas, or at least 10 mole-%, or at least 20 mole-%, or at least 25 mole-%, or at least 30 mole-%, on the same basis. Similarly, a ballast gas may be present in the epoxidation feed gas in a concentration of at most 80 mole-%, relative to the total epoxidation feed gas, or at most 75 mole-%, or at most 70 mole-%, or at most 65 mole-%, on the same basis. In some embodiments, a ballast gas may be present in the epoxidation feed gas in a concentration of from 20 mole-% to 80 mole-%, relative to the total epoxidation feed gas, or from 30 mole-% to 70 mole-%, on the same basis.

Optionally, the epoxidation feed gas may further comprise a reaction modifier. If desired, a reaction modifier may be added to the epoxidation feed gas to increase the selectivity of the epoxidation catalyst. Examples of suitable reaction modifiers may include, but are not limited to, organic chlorides (e.g., $C_1$ to $C_3$ chloro hydrocarbons). Specific examples of suitable organic chlorides include, but are not limited to, methyl chloride, ethyl chloride, ethylene dichloride, vinyl chloride, and a combination thereof.

A reaction modifier may optionally be present in the epoxidation feed gas in a concentration of 0.1 parts per million by volume (ppmv) or greater, relative to the total epoxidation feed gas, or 0.3 ppmv or greater, or 0.5 ppmv or greater, on the same basis. Similarly, a reaction modifier is generally present in the epoxidation feed gas in a concentration of at most 25 ppmv, relative to the total epoxidation feed gas, or at most 22 ppmv, or at most 20 ppmv, on the same basis. In some embodiments, a reaction modifier may be present in the epoxidation feed gas in a concentration of from 0.1 to 25 ppmv, relative to the total epoxidation feed gas, or from 0.3 to 20 ppmv, on the same basis. Typically, as the epoxidation feed gas composition changes and/or as one or more of the operating conditions change, the concentration of reaction modifier in the epoxidation feed gas may also be adjusted so as to maintain the optimum concentration. For additional disclosure regarding reaction modifiers and optimum concentrations thereof, reference may be made to, for example U.S. Pat. Nos. 7,193,094 and 8,546,592, which are incorporated herein by reference.

Optionally, the epoxidation feed gas may be substantially free, and preferably completely free, of a nitrogen-containing reaction modifier. That is to say, the epoxidation feed gas may comprise less than 100 ppm of a nitrogen-containing reaction modifier, preferably less than 10 ppm, more preferably less than 1 ppm, and most preferably 0 ppm of a nitrogen-containing reaction modifier. As used herein, the term "nitrogen-containing reaction modifier" refers to a gaseous compound or volatile liquid that is present as, or capable of forming, nitrogen oxides in oxidizing conditions. Examples of nitrogen-containing reaction modifiers include, but are not limited to, NO, $NO_2$, $N_2O_3$, $N_2O_4$, $N_2O_5$ or any substance capable of forming one of the aforementioned gases under epoxidation conditions (e.g., hydrazine, hydroxylamine, ammonia, organic nitro compounds (such as nitromethane, nitroethane, nitrobenzene, etc.), amines, amides, organic nitrites (such as methyl nitrite), nitriles (such as acetonitrile)), and a combination thereof.

Processes of the present disclosure may further comprise contacting at least a portion of the epoxidation reaction product comprising ethylene oxide with lean absorbent in the presence of an iodide-containing carboxylation catalyst in an ethylene oxide absorber to yield a fat absorbent stream comprising ethylene carbonate and/or ethylene glycol and a recycle gas stream comprising an alkyl iodide impurity. In the ethylene oxide absorber, the epoxidation reaction product is brought into intimate contact with lean absorbent in the presence of an iodide-containing carboxylation catalyst, and optionally a hydrolysis catalyst. Typically, the lean absorbent comprises at least 20 wt % water, and preferably comprises from 20 wt % to 80 wt % water. Preferably, the lean absorbent also comprises ethylene carbonate and/or ethylene glycol.

Suitably, an ethylene oxide absorber comprises an inlet that is in fluid communication with an outlet of an epoxidation reactor, an inlet through which lean absorbent is supplied, and an outlet that is in fluid communication with the recycle gas loop. An example of a suitable ethylene oxide absorber includes a column comprising a plurality of vertically stacked trays, which provide a surface area for the lean absorbent and the epoxidation reaction product to come into contact. Preferably, the column comprises at least 20 trays, more preferably at least 30 trays. Preferably the column comprises less than 100 trays, more preferably less than 70 trays, most preferably less than 50 trays. Suitably, the ethylene oxide absorber may be the sort of reactive absorber described in EP 2178815 or in co-pending application EP 14186273.0.

The temperature in the ethylene oxide absorber is preferably from 50° C. to 160° C., preferably from 80° C. to 150° C., more preferably from 80° C. to 120° C. This is higher than the temperature in a conventional process and is required to promote the carboxylation and hydrolysis reactions. Temperature higher than 160° C. is not preferred as this may reduce the selectivity of the ethylene oxide conversion to ethylene glycol. Both the epoxidation reaction product and the lean absorbent are preferably supplied to the ethylene oxide absorber at temperatures in the range from 50'C to 160° C.

The pressure in the ethylene oxide absorber is from 1 to 4M Pa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

The epoxidation reaction product stream supplied to the ethylene oxide absorber comprises carbon dioxide. However, it is possible that the epoxidation reaction product stream may contain insufficient carbon dioxide to achieve desired levels of carboxylation in the ethylene oxide absorber. Optionally, an additional source of carbon dioxide may be supplied to the ethylene oxide absorber, e.g. recycle carbon dioxide from a finishing reactor, carbon dioxide from a carbon dioxide recovery unit or, at start-up, carbon dioxide from an external source.

In the ethylene oxide absorber, the epoxidation reaction product is contacted with lean absorbent in the presence of an iodide-containing carboxylation catalyst and optionally a hydrolysis catalyst. Preferably, the epoxidation reaction product is contacted with lean absorbent in the presence of both an iodide-containing carboxylation catalyst and a hydrolysis catalyst. The carboxylation and hydrolysis catalysts may be homogeneous and/or heterogeneous. In one embodiment, the epoxidation reaction product is contacted with lean absorbent in the presence of both an iodide-containing carboxylation catalyst and a hydrolysis catalyst, and the lean absorbent comprises the catalysts.

Iodide-containing carboxylation catalysts suitable for use herein may be heterogeneous or homogeneous catalysts. Examples of suitable homogenous iodide-containing carboxylation catalysts include, but are not necessarily limited to, alkali metal iodides, such as potassium iodide, and organic phosphonium iodides or ammonium iodide salts such as tributylmethylphosphonium iodide, tetrabutylphosphonium iodide, triphenylmethylphosphonium iodide, and tributylmethylammonium iodide, and combinations thereof. Examples of suitable heterogeneous iodide-containing carboxylation catalysts include, but are not necessarily limited to, quaternary ammonium and quaternary phosphonium iodides immobilized on silica, quaternary ammonium and quaternary phosphonium iodides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups, and combinations thereof. Preferably the iodide-containing carboxylation catalyst is a homogeneous catalyst, most preferably an organic phosphonium iodide or alkali metal iodide.

Similarly, hydrolysis catalysts suitable for use herein may be heterogeneous or homogeneous catalysts. Examples of suitable homogenous hydrolysis catalysts include, but are not necessarily limited to, basic alkali metal salts, such as potassium carbonate, potassium hydroxide and potassium bicarbonate, and alkali metal metalates, such as potassium molybdate, and combinations thereof. Examples of suitable heterogenous hydrolysis catalysts include, but are not necessarily limited to, metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups, and combinations thereof.

A fat absorbent stream comprising ethylene carbonate and/or ethylene glycol is withdrawn from the ethylene oxide absorber via an outlet, preferably by withdrawing liquid from an outlet at the bottom of the ethylene oxide absorber. Preferably, at least 50% of the ethylene oxide entering the ethylene oxide absorber is converted in the ethylene oxide absorber. Preferably, at least 60%, more preferably at least 70%, even more preferably at least 80%, most preferably at least 90% of the ethylene oxide entering the ethylene oxide absorber is converted in the ethylene oxide absorber. The ethylene oxide may undergo carboxylation, providing ethylene carbonate. The ethylene oxide may undergo hydrolysis, providing ethylene glycol. Additionally, the ethylene carbonate that is produced from the ethylene oxide may undergo hydrolysis, providing ethylene glycol.

Optionally, a portion or all of the fat absorbent stream may be supplied to one or more finishing reactors (e.g., to provide further conversion of any ethylene oxide and/or ethylene carbonate that was not converted in the ethylene oxide absorber). Suitable finishing reactors may include a carboxylation reactor, a hydrolysis reactor, a carboxylation and hydrolysis reactor, and a combination thereof. Supply to one or more finishing reactors is preferred if a significant quantity (e.g. at least 1%) of ethylene oxide or ethylene carbonate is not converted to ethylene glycol in the ethylene oxide absorber.

Having generally described the invention, a further understanding may be obtained by reference to the following examples, which are provided for purposes of illustration and are not intended to be limiting unless otherwise specified.

EXAMPLES

Preparation of Stock Silver Solution:

The description below describes an exemplary procedure for the preparation of a stock silver oxalate/ethylenediamine/water impregnation solution.

A silver-amine-oxalate stock solution was prepared by the following procedure:

In a 5-liter stainless steel beaker, 415 g of reagent-grade sodium hydroxide were dissolved in 2340 ml de-ionized water, and the temperature was adjusted to 50° C.

In a 4-liter stainless steel beaker, 1699 g high purity "Spectropure" silver nitrate was dissolved in 2100 ml de-ionized water, and the temperature was adjusted to 50° C.

The sodium hydroxide solution was added slowly to the silver nitrate solution, with stirring, while maintaining a solution temperature of 50° C. This mixture was stirred for 15 minutes. The pH of the solution was maintained at above 10 by the addition of sodium hydroxide solution as required.

Water was removed from the precipitate created in the mixing step and the conductivity of the water, which contained sodium and nitrate ions, was measured. An amount of fresh de-ionized water equal to the amount removed was added back to the silver solution. The solution was stirred for 15 minutes at 40° C. The process was repeated until the conductivity of the water removed was less than 90 μmho/cm. 1500 ml fresh deionized water was then added. 630 g of high-purity oxalic acid dihydrate were added in approximately 100 g increments. The temperature was kept at 40° C. (±5° C.) and the pH of the solution was monitored during the addition of the last 130 grams of oxalic acid dihydrate to ensure that the pH did not drop below 7.8 for an extended period of time. Water was removed from this mixture to leave a highly concentrated silver-containing slurry. The silver oxalate slurry was cooled to 30° C. 699 g of 92 weight percent ethylenediamine (8% de-ionized water) was then added while maintaining a temperature no greater than 30° C.

Example 1

Preparation of the Absorbent:

Absorbent A was prepared by the following procedure: A 9.3 g aliquot of a stock silver oxalate/ethylenediamine/water impregnation solution, having a specific gravity of 1.554 g/mL, was diluted with 40.6 g deionized water. To this was added 0.643 g potassium carbonate, and the solution was stirred briefly to fully dissolve the salt. 30.0 g of Support A (see Table I below for a description of the 2.5 mm gamma alumina trilobe) was vacuum impregnated with the described solution for 6 minutes. After the vacuum was broken, excess solution was decanted off of the impregnated supports, and the supports were centrifuged for 2 minutes to remove bulk excess liquid. The impregnated supports were dried in rapidly flowing 250° C. air in a vibrating basket, the bottom of which was constructed of fine stainless steel screen. The impregnated supports were then calcined in a ceramic tray under gently flowing air at 375° C. for 25 minutes, and then cooled producing Absorbent A.

The final composition of Absorbent A comprised the following, calculated on the basis of pore volume impregnation: 5 wt % Ag, 0.5 wt % K. These values are relative to the weight of the absorbent.

Absorbent B was prepared by the following procedure: An 18.4 g aliquot of stock silver oxalate/ethylenediamine/water impregnation solution, having a specific gravity 1.571 g/mL, was diluted with 81.6 g deionized water. To this was added 1.28 g potassium carbonate, and the solution was stirred briefly to fully dissolve the salt. This solution was pore volume impregnated to the point of incipient wetness into 11.9 g of Support B (see Table I below for a description of the 1.0 mm spherical alumina). The impregnated support was then dried for 6 minutes in 250° C. gently flowing air in a vibrating basket, the top and bottom of which were constructed of fine stainless steel screens, producing Absorbent B.

The final composition of Absorbent B comprised the following, calculated on the basis of pore volume impregnation: 5 wt % Ag, 0.5 wt % K. These values are relative to the weight of the absorbent.

TABLE I

| Support Properties | | |
| --- | --- | --- |
| Properties | Support A | Support B |
| Size and Shape | 2.5 mm Trilobe | 1.0 mm Sphere |
| Surface Area (m$^2$/g) | 100-150 | 150-170 |
| Minimum pore volume (mL/g) | .88 | 0.45 |

Testing of the Absorbent

Absorbent A:

3.40 g of Absorbent A was loaded into a ¼" internal diameter U-shaped stainless steel microreactor tube, and secured with plugs of glass wool affixed with steel screens at the inlet and the outlet of the bed. A feed stream consisting of 25% v ethylene, 7.3% v oxygen, 1.3% v carbon dioxide, 3 ppmv ethyl chloride, approximately 750 ppbv methyl iodide, approximately 750 ppbv ethyl iodides, balance nitrogen was directed through the guard bed at a flowrate of 800 mL/min, as the guard bed was maintained at a pressure of 285 psig and a temperature of 120° C. The exit gas was periodically analyzed for part-per-billion-level iodides. The point of "breakthrough" was defined as the last gas sample for which less than 2% of the feed stream level of each iodide was detected in the exit gas. For this test, breakthrough occurred at about 481 hours. The point of breakthrough presented an iodide capacity of 27.8 g elemental iodine per liter of guard bed, representing 92.8% of theoretical maximum capacity based on 1:1 iodine:silver stoichiometry.

Absorbent B:

5.27 g of Absorbent B were loaded into a ¼" internal diameter U-shaped stainless steel microreactor tube, and secured with plugs of glass wool affixed with steel screens at the inlet and the outlet of the bed. A feed stream consisting of 25% v ethylene, 7.3% v oxygen, 1.3% v carbon dioxide, 3.0 ppmv ethyl chloride, approximately 5140 ppbv methyl iodide, approximately 4460 ppbv ethyl iodides, balance nitrogen was directed through the guard bed at a flowrate of 800 cc/min, as the guard bed was maintained at a pressure of 285 psig and a temperature of 120° C. The exit gas was periodically analyzed for part-per-billion-level iodides. Again, the point of "breakthrough" was defined as the last gas sample for which less than 2% of the feed stream level of each iodide was detected in the exit gas. For this test, breakthrough occurred at about 126 hours. The point of breakthrough presented an iodide capacity of 46.7 g elemental iodine per liter of guard bed (grams-I/liter-GB), representing 99.0% of theoretical maximum silver utilization based on 1:1 iodine:silver stoichiometry (atoms-I/atoms-Ag).

The data is summarized below in Table II.

TABLE II

| | Support | GB Pkg Density (kg/L) | GB Loading Mass (g) | GB Loading Volume (mL) | Iodides Delivered MeI (ppbv) | Iodides Delivered EtI (ppbv) | Time Prior to Breakthrough (hrs) | Iodide Capacity (g-I/L-GB) | Ag Utilization |
|---|---|---|---|---|---|---|---|---|---|
| Abs. A | Supp. A 2.5 mm TL | 0.51 | 3.40 | 6.67 | 760 | 760 | 481 | 27.8 | 92.8% |
| Abs. B | Supp. B 1 mm Sphere | 0.80 | 5.27 | 6.57 | 5139 | 4462 | 126 | 46.7 | 99.0% |

The results demonstrate that Absorbent B, prepared on 1 mm spherical supports, exhibits more effective silver utilization as compared with the material prepared using the same loading of silver, but prepared on a larger and non-spherical carrier.

Example 2

Preparation of Absorbents C-L:

Absorbents C-L were prepared on support B, and in a manner similar to Absorbent B. The final compositions of Absorbents C-L are provided in Table III.

Testing of Absorbents C-L:

The specified grams of Absorbents C-L were each loaded into a ¼" internal diameter U-shaped stainless steel microreactor tube, and secured with plugs of glass wool affixed with steel screens at the inlet and the outlet of the bed. A feed stream consisting of 25% v ethylene, 7.3% v oxygen, 1.3% v carbon dioxide, 3.0 ppmv ethyl chloride, approximately 2500 ppbv methyl iodide, approximately 2500 ppbv ethyl iodides, balance nitrogen was directed through the guard bed at a flowrate of 800 mL/min, as the guard bed was maintained at a pressure of 295 psig and a temperature of 120° C. The exit gas was periodically analyzed for part-per-billion-level iodides.

TABLE III

| Absorbent | % Ag | % K | Mass (g) | Total Iodides Delivered (ppbv) | Time to Breakthrough (hrs) | Iodide Capacity (g-I/L GB) | Ag Utilization |
|---|---|---|---|---|---|---|---|
| C | 4.0 | 0.5 | 5.15 | 4720 | 182 ± 10 | 42 | 88% |
| D | 4.5 | 0.5 | 5.07 | 5280 | 204 ± 8 | 54 | 100% |
| E | 5.0 | 0 | 5.20 | 5330 | 208 ± 23 | 54 | 90% |
| F | 5.0 | 0.5 | 5.56 | 5030 | 277 ± 12 | 64 | 106% |
| G | 5.0 | 0.5 | 5.27 | 5460 | 228 ± 9 | 60 | 100% |
| H | 5.0 | 1.0 | 5.30 | 5360 | 262 ± 9 | 67 | 112% |
| I | 6.0 | 0.5 | 5.28 | 5490 | 248 ± 5 | 65 | 91% |
| J | 6.0 | 0.5 | 5.28 | 5224 | 261 ± 5 | 66 | 91% |
| K | 7.0 | 0.5 | 5.30 | 5332 | 293 ± 5 | 75 | 89% |
| L | 8.0 | 0.5 | 5.20 | 5310 | 288 ± 12 | 75 | 78% |

The results demonstrate that a guard bed material according to the invention is effective at reducing the amount of an alkyl iodide impurity in a recycle gas stream.

That which is claimed is:

1. A process comprising:
    contacting at least a portion of a recycle gas stream comprising an alkyl iodide impurity with a guard bed material to yield a treated recycle gas stream, wherein the guard bed material comprises a spherical support material having a diameter of less than 2 mm, and deposited on the spherical support material, silver in an amount of from 2% to 10% by weight; and
    contacting an epoxidation feed gas comprising ethylene, oxygen and at least a portion of the treated recycle gas stream with an epoxidation catalyst to yield an epoxidation reaction product comprising ethylene oxide.

2. The process of claim 1, further comprising:
    contacting at least a portion of the epoxidation reaction product comprising ethylene oxide with a lean absorbent in the presence of an iodide-containing carboxylation catalyst to yield a fat absorbent stream comprising ethylene carbonate and/or ethylene glycol and the recycle gas stream comprising the alkyl iodide impurity.

3. The process of claim 1, wherein silver is present in the guard bed material in an amount of from 3% to 9% by weight.

4. The process of claim 1, wherein silver is present in the guard bed material in an amount of from 4% to 8% by weight.

5. The process of claim 1, wherein the guard bed material further comprises at least one metal selected from the group consisting of an alkali metal, an alkaline earth metal, and a combination thereof.

6. The process of claim 5, wherein the at least one metal is an alkali metal selected from the group consisting of sodium, potassium, lithium, rubidium, cesium, and combinations thereof.

7. The process of claim 5, wherein the alkali metal is present in the guard bed material in an amount of from 0.1% to 5% by weight.

8. The process of claim 1, wherein the spherical support material comprises alumina.

9. The process of claim 1, wherein the spherical support material has a diameter of from 0.25 mm to 1.5 mm.

10. The process of claim 1, wherein the spherical support material has a surface area of at least 50 $m^2/g$.

11. The process of claim 1, wherein the treated recycle gas stream comprises no more than 6 ppbv of alkyl iodide.

12. The process of claim 1, wherein the treated recycle gas stream comprises no more than 1 ppbv of alkyl iodide.

13. The process of claim 1, wherein the treated recycle gas stream is supplied to a carbon dioxide absorber before being contacted with the epoxidation catalyst.

14. A reaction system for the production of ethylene carbonate and/or ethylene glycol comprising:
    a recycle gas loop fluidly connected to a source of ethylene and oxygen;
    an epoxidation reactor comprising an epoxidation catalyst, an inlet, and an outlet, wherein the inlet of the epoxidation reactor is fluidly connected to the recycle gas loop;
    an ethylene oxide absorber comprising an iodide-containing carboxylation catalyst, an inlet, and an outlet, wherein the outlet of the epoxidation reactor is fluidly connected to the inlet of the ethylene oxide absorber, the outlet of the ethylene oxide absorber is fluidly connected to the recycle gas loop, and the ethylene oxide absorber is configured to produce a recycle gas stream comprising an alkyl iodide impurity and a fat absorbent stream comprising ethylene carbonate and/or ethylene glycol; and
    a guard bed system comprising an inlet, an outlet, and one or more guard bed vessels comprising a guard bed material, wherein the guard bed material comprises a spherical support material having a diameter of less than 2 mm, and deposited on the spherical support material, silver in an amount of from 2% to 10% by weight, wherein the inlet and the outlet of the guard bed system is fluidly connected to the recycle gas loop, and the guard bed material is configured to remove at least a portion of the alkyl iodide impurity from at least a portion of the recycle gas stream.

15. The reaction system of claim 14, further comprising a carbon dioxide absorber fluidly connected to the recycle gas loop.

16. The reaction system of claim 14, wherein the guard bed system comprises two or more guard bed vessels.

* * * * *